(12) United States Patent
Groenendaal et al.

(10) Patent No.: US 6,927,298 B2
(45) Date of Patent: Aug. 9, 2005

(54) 3,4-ALKYLENEDIOXYTHIOPHENEDIOXIDE COMPOUNDS AND POLYMERS COMPRISING MONOMERIC UNITS THEREOF

(75) Inventors: Bert Groenendaal, Sinaai (BE); Frank Louwet, Diepenbeek (BE); Hieronymus Andriessen, Beerse (BE)

(73) Assignee: Agfa-Gevaert, Mortsel (BE)

( * ) Notice: Subject to any disclaimer, the term of this patent is extended or adjusted under 35 U.S.C. 154(b) by 168 days.

(21) Appl. No.: 10/649,761

(22) Filed: Aug. 27, 2003

(65) Prior Publication Data

US 2004/0097741 A1 May 20, 2004

Related U.S. Application Data

(60) Provisional application No. 60/418,640, filed on Oct. 15, 2002.

(30) Foreign Application Priority Data

Sep. 2, 2002 (WO) .............................. PCT/EP02/09887

(51) Int. Cl.[7] .................. C07D 333/64; C07D 333/36; C08G 75/00; C08G 65/34
(52) U.S. Cl. ......................... 549/53; 549/63; 528/373; 526/256
(58) Field of Search .................... 549/53, 60; 528/373; 526/256

(56) References Cited

U.S. PATENT DOCUMENTS

| | | | | |
|---|---|---|---|---|
| 5,593,812 A | * | 1/1997 | Babich et al. | 430/270.1 |
| 5,753,412 A | * | 5/1998 | Babich et al. | 430/270.1 |
| 5,770,345 A | * | 6/1998 | Babich et al. | 430/270.1 |
| 6,852,830 B2 | * | 2/2005 | Groenendaal et al. | 528/373 |

FOREIGN PATENT DOCUMENTS

| | | |
|---|---|---|
| DE | 41 18 704 A1 | 12/1992 |
| EP | 0 257 573 A1 | 3/1988 |
| EP | 0 339 340 A2 | 11/1989 |
| EP | 0 440 957 A2 | 8/1991 |
| EP | 0 686 662 A2 | 12/1995 |
| EP | 1 041 132 A2 | 10/2000 |

OTHER PUBLICATIONS

Barbarella et al.; *J. Org. Chem.*, 63, 5497–5506 (1998).
Furukawa et al; *Heterocycles*, 34 (6), 1085–1088 (1992).
Mock; *J. of the Am. Chem. Soc.*, 92, 7610–7612 (Dec. 30, 1970).
International Search Report for PCT/EP02/09887 (Jun. 2, 2003).
Dallacker et al; *Chem. Ber.*, 108, 569–575 (1975).

* cited by examiner

*Primary Examiner*—Deborah C. Lambkin
(74) *Attorney, Agent, or Firm*—Leydig, Voit & Mayer, Ltd.

(57) ABSTRACT

A 3,4-alkylenedioxythiophenedioxide compound represented by formula (I):

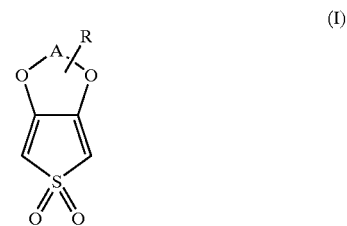

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group; a polymer comprising monomeric units represented by formula (I); an aqueous dispersion of a polymer comprising monomeric units corresponding to at least one compound according to formula (I) and a polyanion; a chemical polymerization process for preparing the aqueous dispersion comprising the steps of: (i) providing a solution of a polyanion; (ii) adding a compound according to formula (I) and a thiophene or pyrrole compound to the solution provided in step (i); and (iii) adding an oxidizing or reducing system to the mixture provided in step (ii); a printable paste containing the aqueous dispersion; an electroconductive layer containing the polymer; the use of the electroconductive layer in a light emitting diode; an antistatic layer containing the polymer; and an electroconductive pattern and a process for preparing the electroconductive pattern.

21 Claims, 1 Drawing Sheet

Figure 1:

3,4-ALKYLENEDIOXYTHIOPHENEDIOXIDE COMPOUNDS AND POLYMERS COMPRISING MONOMERIC UNITS THEREOF

This application claims the benefit of U.S. Provisional Application No. 60/418,640 filed Oct. 15, 2002, which is incorporated by reference. In addition, this application claims the benefit of International Application No. PCT/EP 02/09887 filed Sep. 2, 2002, which is also incorporated by reference.

FIELD OF THE INVENTION

The present invention concerns new 3,4-alkylenedioxythiophenedioxide compounds and polymers comprising monomeric units thereof.

BACKGROUND OF THE INVENTION

In 1970, Mock in Journal of the American Chemical Society, volume 92, page 7610 disclosed 2,5-di-tert-butyl-thiophene-1,1-dioxide. In 1992, Furukawa et al. in Heterocycles, volume 34, pages 1085–1088, disclosed 2,5-bis(trimethylsilyl)-thiophene-1,1-dioxide. In 1998, Barbarella et al. in Journal of Organic Chemistry, volume 63, page 5497, disclosed 2-(dimethyl-tert-butyl-silyl)-5-bromo-thiophene-1,1-dioxide, 2-n-hexyl-5-bromo-thiophene-1,1-dioxide, 2,5-dibromo-3,4-dihexyl-thiophene-1,1-dioxide and 2,5-di-n-hexyl-thiophene-1,1-dioxide. EP-A 1 041 132 discloses a luminescent organic material for light-emitting devices, characterized by comprising at least one thienyl-S,S-dioxide unit. Specific thiophene-1,1-dioxide compounds are disclosed: 2,5-diphenyl-thiophene-1,1-dioxide, 3,4-dihexyl-2,5-diphenyl-thiophene-1,1-dioxide, 3,4-dineopentyl-2,5-diphenyl-thiophene-1,1-dioxide, 3,4-dimethyl-2,5-diphenyl-thiophene-1,1-dioxide, 3,4-dihexyl-2,5-bis(diphenyl)-thiophene-1,1-dioxide and 2,5-trimethylsilyl-thiophene-1,1-dioxide.

Polythiophenes have been studied extensively due to their interesting electrical and/or optical properties. Polythiophenes become electrically conducting upon chemical or electrochemical oxidation or reduction.

In 1975 Dallacker et al. in Chemische Berichte, volume 108, pages 569–575, disclosed methylenation experiments with 3,4-dihydroxy compounds of diethyl thiophene-, furan-, phenyl-, and 1-(ethoxycarbonylmethyl)-2,5-pyrroledicarboxylate. Methylenations with 3,4-dihydroxy-2,5-thiophenedicarboxylate only led to the 3,4-methylenedioxythiophene derivatives, 3,4-methylenedioxy-2,5-thiophenedicarboxylic acid diethyl ester and 3,4-methylenedioxy-2,5-thiophenedicarboxylic acid diethyl ester-S,S-dioxide respectively, with formation of diethyl dithieno[3,4-b:3',4'-g]-tetroxecin-1,3,7,9-tetreacarboxylate as a by-product.

EP-A 257 573 discloses an intrinsically electrically conductive polymer, wherein through connection in the 2-position and/or the 5-position are coupled to one another, statistically averaged from 60 to 100% by weight structural units, which are derived from at least one monomer of the formula (1):

in which $R^1$ is a C1–C2-alkoxy group or —O(CH$_2$CH$_2$O)$_n$CH$_3$ with n=1 to 4 and $R^2$ is a hydrogen atom, a C$_{1-12}$-alkyl group, a C$_{1-12}$-alkoxy group or —O(CH$_2$CH$_2$O)$_n$CH$_3$ with n=1 to 4, or $R^1$ and $R^2$ together are —O(CH$_2$)$_m$—CH$_2$— or —O(CH$_2$)$_m$—O— with m=1 to 12, 0 to 40% by weight structural units, which are derived from at least one monomer of the formula (2):

wherein $R^4$ and $R^5$ are independently of one another a hydrogen atom, a halogen atom, a C$_{1-12}$-alkyl group or aryl or together with C-atoms connected to them form an aromatic ring, $R^3$ and $R^6$ independently of one another represent a hydrogen atom or $R^3$ together with $R^4$ and the C-atoms connected to them or $R^5$ together with $R^6$ and the C-atoms connected to them each form an aromatic ring, X represents an oxygen atom, a sulphur atom, a =NH group, a =N-alkyl group or a =N-aryl group, 0 to 40% by weight structural units, which are derived from at least one monomer of formula (3):

where $R^7$, $R^8$, $R^9$ and $R^{10}$ independently of one another represent a hydrogen atom, a C$_{1-12}$-alkyl group, a C$_{1-12}$-alkoxy group or an aryl group, Y and Z independently of one another represent an oxygen atom, a sulphur atom, a =NH group, a =N-alkyl group or a =N-aryl group, $R^{11}$ represents an arylene group, a heteroarylene group or a conjugated system of the formula (CH=CH)$_o$, wherein o is 1, 2 or 3, 0 to 40% by weight structural units, which are derived from at least one monomer of formula (4):

wherein $R^{12}$ and $R^{13}$ independently of one another represent a hydrogen atom, a halogen atom, a C$_{1-12}$-alkyl group, a C$_{1-12}$-alkoxy group, a C$_{1-4}$-alkylamino group or a C$_{1-4}$-acylamino group, $R^{14}$ represents a halogen atom, a C$_{1-12}$-alkyl group, a C$_{1-12}$-alkoxy group, a C$_{1-4}$alkylamino group or a C$_{1-4}$-acylamino group and X has the meaning given above, wherein the polymer in the oxidized form is completely soluble in dipolar aprotic solvents at 25° C. and solutions with a content of at least 0.1 g of the polymer in 100 mL solvent at 25° C. are obtained.

EP-A 339 340 discloses a polythiophene containing structural units of the formula:

in which A denotes an optionally substituted $C_{1-4}$-alkylene group and its preparation by oxidative polymerization of the corresponding thiophene.

EP-A 440 957 discloses dispersions of polythiophenes, constructed from structural units of formula (I):

in which $R^1$ and $R^2$ independently of one another represent hydrogen or a $C_{1-4}$-alkyl group or together form an optionally substituted $C_{1-4}$-alkylene residue, in the presence of polyanions.

EP-A-686 662 discloses mixtures of A) neutral polythiophenes with the repeating structural unit of formula (I), in which $R^1$ and $R^2$ independently of one another represent hydrogen or a $C_{1-4}$-alkyl group or together represent an optionally substituted $C_{1-4}$-alkylene residue, preferably an optionally with alkyl group substituted methylene, an optionally with $C_{1-12}$-alkyl or phenyl group substituted 1,2-ethylene residue or a 1,2-cyclohexene residue, and B) a di- or polyhydroxy- and/or carboxy groups or amide or lactam group containing organic compound; and conductive coatings therefrom which are tempered at elevated temperature, preferably between 100 and 250° C., during preferably 1 to 90 seconds to increase their resistance preferably to <300 ohm/square.

PEDOT/PSS layers have been widely used in light emitting diodes as an intermediate layer between a indium tin dioxide layer and a hole transporting layer. However, the conductivity of such layers is is too high and so-called cross-talk arises resulting in short-circuiting.

There is a need for hole-conducting intermediate layers with a similar work function, but reduced electrical conductivity.

OBJECTS OF THE INVENTION

It is therefore an aspect of the present invention to provide polymers which exhibit high visible light transmittances, good processability and similar work functions but reduced electrical conductivities compared with poly(3,4-alkylenedioxythiophene)'s.

It is also a further aspect of the present invention to provide an electroconductive pattern.

Further aspects and advantages of the invention will become apparent from the description hereinafter.

SUMMARY OF THE INVENTION

It has been surprisingly found that copolymerizing EDOT-dioxide with EDOT reduces the molecular weight of copolymer produced in the presence of PSS. It surprisingly appears that EDOT-dioxide may act as a chain stopper in the copolymerization process resulting in a reduced molecular weight, reduced conjugation length and reduced conductivity, although the work function as measured by UPS measurements is unaffected. This makes this copolymer a very interesting candidate to replace PEDOT/PSS-layers in organic light emitting diodes so-called OLED's due to so-called reduced cross-talk i.e. lateral electrical conductivity.

Aspects of the present invention are realized with 3,4-alkylenedioxythiophenedioxide compound represented by formula (I):

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

Aspects of the present invention are also provided by a polymer comprising monomeric units of at least one of the above-mentioned compounds.

Aspects of the present invention are also provided by an aqueous dispersion of a polymer comprising monomeric units of at least one of the above-mentioned compounds and a polyanion.

Aspects of the present invention are also provided by a chemical polymerization process for preparing the above-mentioned aqueous dispersion comprising the steps of: (i) providing a solution of a polyanion; (ii) adding the above-mentioned compound and a thiophene or a pyrrole compound to the solution provided in step (i); and (iii) adding an oxidizing or reducing system to the mixture provided in step (ii).

Aspects of the present invention are also provided by the use of the above-mentioned dispersion for coating an object.

Aspects of the present invention are also provided by a printable paste containing the above-mentioned aqueous dispersion.

Aspects of the present invention are also provided by an electroconductive layer containing the above-mentioned polymer.

Aspects of the present invention are also provided by the use of the above-mentioned electroconductive layer in a light emitting diode.

Aspects of the present invention are also provided by an antistatic layer containing the above-mentioned polymer.

Aspects of the present invention are also provided by an electroconductive pattern comprising a polymer containing 3,4-alkylenedioxythiophene monomer units and a polymer containing 3,4-alkylenedioxythiophenedioxide monomer units.

Aspects of the present invention are also provided by a process for preparing the above-mentioned electroconductive pattern comprising the steps of: providing a layer of a polymer containing 3,4-alkylenedioxythiophene monomer units; and pattern-wise oxidizing the polymer containing 3,4-alkylenedioxythiophene monomer units to polymers containing 3,4-alkylenedioxythiophenedioxide monomer units.

Further aspects of the present invention are disclosed in the dependent claims.

DETAILED DESCRIPTION OF THE INVENTION

FIG. 1 is a schematic representation of a side view and a top view of the layer configuration used in devices 1 to 3 and the circuit used for obtaining electroluminescence in which:

A represents a poly(ethylene terephthalate) support;
B represents an sputtered ITO layer;
C represents an electron blocking layer;
D represents an electroluminescent layer containing ZnS:Cu nanoparticles and a binder;
E represents an evaporated aluminium electrode
F represents conductive silver paste dots for contacting
G represents IV-power source (Power Supply ES 030-5 of Delta Elektronica)
H represents electric conductive copper wires
I indicates the first layer
II indicates the second layer
III indicates the third layer

DEFINITIONS

The term $C_{1-5}$-alkylene group represents methylenedioxy, 1,2-ethylenedioxy, 1,3-propylenedioxy, 1,4-butylenedioxy and 1,5-pentylenedioxy groups.

The term alkyl means all variants possible for each number of carbon atoms in the alkyl group i.e. for three carbon atoms: n-propyl and isopropyl; for four carbon atoms: n-butyl, isobutyl and t-butyl; for five carbon atoms: n-pentyl, 1,1-dimethyl-propyl, 2,2-dimethylpropyl and 2-methyl-butyl etc.

The term 3,4-alkylenedioxythiophene compound as used in disclosing the present invention means a thiophene molecule substituted with an optionally substituted oxy-alkyl-oxy bridge between the 3- and 4-positions thereof.

The term 3,4-alkylenedioxythiophenedioxide compound as used in disclosing the present invention means a thiophene molecule in which the sulphur atom is directly bonded to two oxygen atoms and in which the thiophene molecule is substituted with an optionally substituted oxy-alkyl-oxy bridge between the 3- and 4-positions thereof e.g. 2,3-dihydro-thieno[3,4-b][1,4]dioxine 6,6-dioxide:

The term polymer as used in disclosing the present invention includes homopolymers, copolymers, terpolymers, graft copolymers and block copolymers.

The term aqueous dispersion of a polymer means that particles of the polymer are suspended in the aqueous medium.

The term aqueous for the purposes of the present invention means containing at least 60% by volume of water, preferably at least 80% by volume of water, and optionally containing water-miscible organic solvents such as alcohols e.g. methanol, ethanol, 2-propanol, butanol, iso-amyl alcohol, octanol, cetyl alcohol etc.; glycols e.g. ethylene glycol; glycerine; N-methyl pyrrolidinone; methoxypropanol; and ketones e.g. 2-propanone and 2-butanone etc.

The term conductive layer as used in disclosing the present invention includes both electroconductive coatings and antistatic layers.

The term electroconductive means having a surface resistance below $10^6$ Ω/square.

The term antistatic means having a surface resistance in the range from $10^6$ to $10^{11}$ Ω/square meaning it cannot be used as an electrode.

The term "conductivity enhancement" refers to process disclosed in EP-A 686 662 in which the conductivity is enhanced e.g. by contact with high boiling point liquids such as di- or polyhydroxy and/or carboxy groups or amide or lactam group containing organic compound optionally followed by heating at elevated temperature, preferably between 100 and 250° C., during preferably 1 to 90 seconds, results in conductivity increase. Alternatively in the case of aprotic compounds with a dielectric constant $\geq 15$, e.g. N-methylpyrrolidinone, temperatures below 100° C. can be used as disclosed in EP-A 1 003 179. Such conductivity enhancement is observed with polythiophenes and can take place during the preparation of the outermost layer or subsequently. Particularly preferred liquids for such treatment are N-methyl-pyrrolidinone and diethylene glycol such as disclosed in EP-A 686 662 and EP-A 1 003 179.

PEDOT as used in the present disclosure represents poly(3,4-ethylenedioxythiophene).

EDOT as used in the present disclosure represents 3,4-ethylenedioxythiophene.

ADOT as used in the present disclosure represents 3,4-alkylenedioxythiophene.

ADOT-dioxide as used in the present disclosure represents 3,4-alkylenedioxythiophenedioxide.

PSS as used in the present disclosure represents poly(styrenesulphonic acid) or poly(styrenesulphonate).

PET as used in the present disclosure represents poly(ethylene terephthalate).

3,4-Alkylenedioxythiophenedioxide Compound

According to a first embodiment of the 3,4-alkylenedioxythiophenedioxide compound, according to the present invention, the 3,4-alkylenedioxythiophenedioxide compound is represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group), an optionally substituted aryl group or an optionally substituted acyl group.

According to a second embodiment of the 3,4-alkylenedioxythiophenedioxide compound, according to the present invention, the 3,4-alkylenedioxythiophene compound is represented by formula (I)

(I)

in which: A represents a $C_{1-5}$-alkylene bridge; and R represents an optionally substituted $C_{6-20}$-alkyl group.

According to a third embodiment of the 3,4-alkylenedioxythiophenedioxide compound, according to the present invention, the 3,4-alkylenedioxythiophenedioxide compound is represented by formula (I):

(I)

in which: A represents a $C_{1-5}$-alkylene bridge; and R represents an optionally substituted $C_{8-18}$-alkyl group.

According to a fourth embodiment of the 3,4-alkylenedioxythiophenedioxide compound, according to the present invention, the 3,4-alkylenedioxythiophenedioxide compound is represented by formula (I):

(I)

in which: A represents a $C_{1-5}$-alkylene bridge; and R represents a substituted $C_{2-24}$-alkyl, $C_{3-18}$-cycloalkyl, $C_{1-18}$-alkoxy or aryl group containing at least one substituent selected from the group consisting of an ether, an ester, an amide, a sulphonate, a phosphonate, a halogen and a hydroxy group.

According to a fifth embodiment of the 3,4-alkylenedioxythiophenedioxide compound, according to the present invention, the 3,4-alkylenedioxythiophenedioxide compound is 2,3-dihydrothieno[3,4-b][1,4]dioxine 6,6-dioxide.

3,4-Alkylenedioxythiophenedioxide compounds can be prepared from the corresponding thiophene compounds by oxidation by peroxides such as m-chloroperoxybenzoic acid (m-CPBA), dimethyldioxirane and $HOF \cdot CH_3CN$ [see references in Journal of Organic Chemistry, volume 63, pages 5497–5506 (1998)].

3,4-Alkylenedioxythiophenedioxide compounds were found not to homopolymerize either electrochemically or chemically.

Polymer comprising 3,4-alkylenedioxythiophenedioxide monomer units

According to a first embodiment of the polymer, according to the present invention, the polymer further comprises monomeric units of at least one thiophene or pyrrole compound.

According to a second embodiment of the polymer, according to the present invention, the polymer further comprises monomeric units of at least one 3,4-alkylenedioxythiophene compound.

According to a third embodiment of the polymer, according to the present invention, the polymer further comprises at least one 3,4-alkylene-dioxythiophenedioxide compound represented by formula (II):

(II)

in which: A' represents a $C_{1-5}$-alkylene bridge; R' represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

According to a fourth embodiment of the polymer, according to the present invention, the polymer further comprises monomeric units of at least one 3,4-alkylenedioxythiophene compound represented by formula (II):

(II)

in which: A' represents a $C_{1-5}$-alkylene bridge; R' represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group), an optionally substituted aryl group or an optionally substituted acyl group.

According to a fifth embodiment of the polymer, according to the present invention, the polymer further comprises monomeric units of at least one 3,4-alkylenedioxythiophene compound represented by formula (II):

(II)

in which: A' represents a $C_{1-5}$-alkylene bridge; and R' represents an optionally substituted $C_{6-20}$-alkyl group.

According to a sixth embodiment of the polymer, according to the present invention, the polymer further comprises monomeric units of at least one 3,4-alkylenedioxythiophene compound represented by formula (II):

(II)

in which: A' represents a $C_{1-5}$-alkylene bridge; and R' represents an optionally substituted $C_{8-18}$-alkyl group.

According to a seventh embodiment of the polymer, according to the present invention, the polymer further comprises monomeric units of at least one 3,4-alkylenedioxythiophene compound represented by formula (II):

(II)

in which: A' represents a $C_{1-5}$-alkylene bridge; and R' represents an optionally substituted $C_{2-24}$-alkyl, $C_{3-18}$-cycloalkyl, $C_{1-18}$-alkoxy or an optionally substituted aryl group contains at least one substituent selected from the group consisting of an ether, an ester, an amide, a sulphonate, a phosphonate, a halogen and a hydroxy group.

According to an eighth embodiment of the polymer, according to the present invention, the polymer is a copolymer of 3,4-ethylenedioxythiophene with a 3,4-alkylenedioxythiophenedioxide compound.

According to a ninth embodiment of the polymer, according to the present invention, the polymer is a copolymer of 3,4-ethylenedioxythiophene with 2,3-dihydro-thieno[3,4-b][1,4]dioxine 6,6-dioxide.

According to a tenth embodiment of the polymer, according to the present invention, the polymer is a copolymer of at least one 3,4-alkylenedioxythiophene compound with at least one 3,4-alkylenedioxythiophenedioxide compound and the at least one 3,4-alkylenedioxythiophene compound is selected from the group consisting of: 3,4-ethylenedioxythiophene, 3,4-propylenedioxythiophene, 3,4-dihydro-2H-thieno[3,4-b][1,4]dioxin-2-yl)methanol, 3,4-dihydro-2H-thieno[3,4-b][1,4]dioxepin-3-ol, (2,3-dihydro-thieno[3,4-b][1,4]dioxin-2-yl-methoxy)-acetic acid, 2-{2-[2-(2-methoxy-ethoxy)-ethoxy]-ethoxymethyl}-2,3-dihydro-thieno[3,4-b][1,4]dioxine and 4-(2,3-dihydro-thieno[3,4-b][1,4]dioxin-2-ylmethoxy)-butane-1-sulphonic acid sodium salt.

Thiophene compounds according to formula (II), according to the present invention, can be prepared by known methods such the transetherification reaction disclosed in DE 3804522 and in HOUBEN-WEYL, volume VI/3, part 3, pages 171–173 (1971) using a thiophene derivative such as 3,4-dimethoxythiophene, or the double Williamson reaction as disclosed in 1994 in Electrochimica Acta in volume 39, pages 1345–1347 using a thiophene derivative such as the dimethyl ester of 3,4-dihydroxythiophene-2,5-dicarboxylic acid.

Homopolymers of 3,4-alkylenedioxythiophenedioxide compounds could not be prepared by the inventors by electrochemical or chemical polymerization, but could be prepared from homopolymers of 3,4-alkylenedioxythiophene compounds by oxidation with oxidation with oxidizing agents such as meta-chloroperbenzoic acid, see INVENTION EXAMPLES 6–21.

Aqueous Dispersions

According to a first embodiment of the aqueous dispersion, according to the present invention, the polymer further comprises monomeric units of at least one thiophene or pyrrole compound.

According to a second embodiment of the aqueous dispersion, according to the present invention, the polymer further comprises monomeric units of at least one 3,4-alkylenedioxythiophene compound.

According to a third embodiment of the aqueous dispersion, according to the present invention, the polyanion is poly(styrenesulphonate).

Polyanion Compound

The polyanion compounds for use in the dispersion according to the present invention are disclosed in EP-A 440 957 and include polymeric carboxylic acids, e.g. polyacrylic acids, polymethacrylic acids, or polymaleic acids and polysulphonic acids, e.g. poly(styrenesulphonic acid). These polycarboxylic acids and polysulphonic acids can also be copolymers of vinylcarboxylic acids and vinylsulphonic acids with other polymerizable monomers, e.g. acrylic acid esters, methacrylic acid esters and styrene.

Chemical Polymerization Process

Aspects of the present invention are also provided by a chemical polymerization process for preparing an aqueous dispersion of a polymer comprising at least one 3,4-alkylenedioxythiophenedioxide compound and a polyanion comprising the steps of: (i) providing a solution of the polyanion; (ii) adding a 3,4-alkylenedioxythiophenedioxide compound and a thiophene or pyrrole compound to the solution provided in step (i); and (iii) adding an oxidizing or reducing system to the mixture provided in step (ii).

According to a first embodiment of the chemical polymerization process, according to the present invention, the thiophene or pyrrole compound is a 3,4-alkylenedioxythiophene compound.

According to a second embodiment of the chemical polymerization process, according to the present invention, inexpensive and easily accessible oxidation agents such as iron(III) salts such as $FeCl_3$, the iron(III) salts of organic acids, e.g. $Fe(OTs)_3$, $H_2O_2$, $K_2Cr_2O_7$, alkali and ammonium persulphates, alkali perborates and potassium permanganate are used in the oxidative polymerization.

Theoretically the oxidative polymerization of thiophenes requires 2.25 equivalents of oxidation agent per mole thiophene of formula (I) [see e.g. J. Polymer Science Part A Polymer Chemistry, volume 26, pages 1287–1294 (1988)]. In practice an excess of 0.1 to 2 equivalents of oxidation agent is used per polymerizable unit. The use of persulphates and iron(III) salts has the great technical advantage that they do not act corrosively. Furthermore, in the presence of particular additives oxidative polymerization of the thiophene compounds according to formula (I) proceeds so slowly that the thiophenes and oxidation agent can be brought together as a solution or paste and applied to the substrate to be treated. After application of such solutions or pastes heating of the coated substrate accelerates the oxidative polymerization as disclosed in U.S. Pat. No. 6,001,281 and WO 00/14139 herein incorporated by reference.

Reductive polymerization can be performed using the Stille (organotin) or Suzuki (organoboron) routes described in 2002 by Appperloo et al. in Chem. Eur. Journal, volume 8, pages 2384–2396, and as disclosed in 2001 in Tetrahedron Letters, volume 42, pages 155–157 and in 1998 in Macromolecules, volume 31, pages 2047–2056 respectively or with nickel complexes as disclosed in 1999 in Bull. Chem. Soc. Japan, volume 72, page 621 and in 1998 in Advanced Materials, volume 10, pages 93–116.

Electroconductive Pattern

Aspects of the present invention are provided by an electroconductive pattern comprising a polymer containing 3,4-alkylenedioxythiophenedioxide monomer units.

3,4-alkylenedioxythiophene monomer units can be oxidized to 3,4-alkylenedioxythiophen-1,1-dioxide units by oxidation by peroxides such as m-chloroperoxybenzoic acid (m-CPBA), dimethyldioxirane and $HOF.CH_3CN$ [see references in Journal of Organic Chemistry, volume 63, pages 5497–5506 (1998)].

According to a first embodiment of the electroconductive pattern, according to the present invention, the electroconductive pattern is obtainable using a process comprising the steps of: providing a layer of a polymer containing 3,4-alkylenedioxythiophene monomer units; and pattern-wise oxidizing the polymer containing 3,4-alkylenedioxythiophene monomer units to polymers containing 3,4-alkylenedioxythiophenedioxide monomer units. A suitable oxidizing agent is meta-chloroperbenzoic acid, also known as meta-chloroperoxybenzoic acid.

Support

A transparent or translucent support suitable for use with the electroconductive or antistatic layers, according to the present invention, may be transparent or translucent, rigid or flexible and consist of paper, polymer film, glass, ceramic, a glass-polymer laminate, a polymer laminate, a thermoplastic polymer or a duroplastic polymer. Examples of thin flexible supports are those made of a cellulose ester, cellulose triacetate, polypropylene, polycarbonate and polyester, with poly(ethylene terephthalate) or poly(ethylene naphthalene-1,4-dicarboxylate) being particularly preferred.

Industrial Application

Polymers comprising monomeric units of at least one 3,4-alkylenedioxythiophenedioxide compound exhibit high visible light transmittances, good processability and similar work functions but reduced electrical conductivities compared with PEDOT/PSS. Such thiophene polymers can be applied to a wide variety of rigid and flexible substrates and are particularly suitable for flexible substrates such as plastic sheeting, which can be substantially bent and deformed without the thiophene polymer layer losing its electrical conductivity.

Such thiophene polymers can, for example, be utilized in photovoltaic devices, batteries, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in electrochromic devices, in sensors for organic and bio-organic materials, in field effect transistors, in printing plates, in conductive resin adhesives and in free-standing electrically conductive films [see also chapter 10 of Handbook of Oligo- and Polythiophenes, Edited by D. Fichou, Wiley-VCH, Weinheim (1999)].

The invention is illustrated hereinafter by way of comparative and invention examples. The percentages and ratios given in these examples are by weight unless otherwise indicated.

SYNTHESIS OF 3,4-ALKYLENEDIOXYTHIOPHENEDIOXIDE COMPOUNDS

Synthesis of 2,3-dihydro-thieno[3,4-b][1,4]dioxine 6,6-dioxide (M1)

A solution of 3,4-ethylenedioxythiophene (EDOT, 20.0 g, 0.14 mol) in methylene chloride (140 mL) was cooled to 0° C., blanketed by nitrogen. m-Chloroperoxybenzoic acid (ca. 70%, 104 mL, 3.0 equivalents) was dissolved in methylene chloride (850 mL) and this solution was added dropwise to the EDOT solution over a period of 90 min. After addition the reaction mixture was stirred for another 30 minutes at 25° C. after which 2,2'-thiodiethanol (9.5 mL) was added. Stirring was continued for another 10 minutes. Then sodium bicarbonate (40 g) in deionized water (500 mL) was added to the reaction mixture and the two-phase system was vigorously shaken. The organic phase was separated, washed with another portion of aqueous sodium bicarbonate solution, washed with hydrochloric acid (1M) and finally washed with a saturated aqueous sodium chloride solution. The resulting organic solution was then filtered over a layer of silica gel and concentrated. Subsequently methanol was added and the precipitated product was filtered. Finally, the product was recrystallized from ethanol/deionized water (60/40) resulting in pure 2,3-dihydro-thieno[3,4-b][1,4] dioxine 6,6-dioxide as demonstrated by NMR spectroscopy, mass spectroscopy and FT-IR spectroscopy.

PREPARATION OF 3,4-ALKYLENEDIOXYTHIOPHENE-HOMOPOLYMERS

COMPARATIVE EXAMPLE 1

At 25° C., 562.5 g of a 5.6% by weight aqueous solution of poly(styrenesulphonic acid) [PSS] ($M_n$=ca. 40,000; $M_w$=290,000; degree of sulphonation >90%), 2437.5 g of deionized water and 12.78 g (90 mmol) EDOT were mixed in a 4L reaction vessel equipped with a stirrer. 0.225 g $Fe_2(SO_4)_3.9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated twice with ion exchanger (300 mL Lewatit™ S100MB+500 mL Lewatit™ M600MB from BAYER). The resulting mixture was additionally thermally treated at 95° C. for 2 h and the resulting viscous mixture treated with high shear (microfluidizer at 600 Bar). 1800 g of a 1.09% by weight blue dispersion of P1 resulted.

COMPARATIVE EXAMPLE 2

At 25° C., 438.239 of a 5.99% by weight aqueous solution of poly(styrenesulphonic acid)[PSS] ($M_n$=ca. 40,000; $M_w$=290,000; degree of sulphonation >90%) and 2061.77 g deionized water were mixed in a 4 L reaction vessel equipped with a stirrer and a nitrogen inlet. After bubbling nitrogen through this mixture for 30 minutes, 12.78 g (90 mmol) of EDOT were added to this solution. 0.225 g $Fe_2(SO_4)_3$ $9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated twice with ion exchanger (300 mL Lewatit™ S100MB+500 mL Lewatit™ M600MB from BAYER). The resulting mixture was additionally thermally treated at 95° C. for 2 h and the resulting viscous mixture treated with high shear (microfluidizer at 600 Bar). This procedure yielded 1950 g of a 1.02% by weight blue dispersion of P2.

COMPARATIVE EXAMPLE 3

At 25° C., 438.23 g of a 5.99% by weight aqueous solution of poly(styrene sulphonic acid) [PSS] ($M_n$=ca. 40,000; $M_w$=290,000; degree of sulphonation >90%) were mixed with 2061.77 g of deionized water in a 4 L reaction vessel equipped with a stirrer and a nitrogen inlet. After bubbling nitrogen purging through this mixture for 30 minutes, 12.78 g (90 mmol) of EDOT was added. 0.225 g $Fe_2(SO_4)_3$ $9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated twice with ion exchanger (300 mL Lewatit™ S100 MB+500 mL Lewatit™ M600MB). The resulting mixture was additionally thermally treated at 95° C. for 2 h and the resulting viscous mixture was treated with high shear (microfluidizer at 600 Bar). This procedure yielded 1840 g of a 1.03% by weight blue dispersion of P3.

Preparing Electroconductive Layers with Dispersions Based on the Dispersions of Comparative Examples 1 to 3

Coating dispersions were produced by adding 3-glycidoxypropyltrimethoxysilane, ZONYL™ FSO100, a copolymer latex of vinylidene chloride, methyl acrylate and itaconic acid (88/10/2) and N-methyl pyrrolidinone to the dispersions of COMPARATIVE EXAMPLES 1 to 3 so as to produce layers, upon doctor blade-coating onto a subbed 175 µm poly(ethylene terephthalate) support and drying at 45° C. for 3.5 minutes, with the following composition:

| | |
|---|---|
| PEDOT | 28.9 mg/m² |
| [PEDOT)/PSS | 100 mg/m²] |
| ZONYL ™ FSO100 | 8 mg/m² |
| 3-glycidoxypropyl-trimethoxysilane | 100 mg/m² |
| copolymer latex of vinylidene chloride, methyl acrylate and itaconic acid (88/10/2) | 100 mg/m² |
| N-methyl pyrrolidinone | 2 mL/m² |

Characterization of Electroconductive Layers Prepared with Dispersions Based on Dispersions of Comparative Examples 1 to 3

The optical density of the layers was determined by measuring a stack of 10 strips in transmission with a MacBeth™ TD904 densitometer using a visible filter and then obtaining therefrom the optical density of a single strip. The values given in Table 1 include the optical density of the PET-support.

The surface resistance of the layers was measured in a room conditioned to a temperature of 25° C. and 30% relative humidity by contacting the printed layer with parallel copper electrodes each 35 mm long and 35 mm apart capable of forming line contacts, the electrodes being separated by a Teflon™ insulator. This enabled direct measurement of the surface resistance to be realized. The results are also given in Table 1.

The layers were then exposed to artificial sunlight (provided by a xenon lamp) through a glass filter in an Atlas Material Testing Technology BV, SUNTEST™ CPS apparatus according to DIN 54 004. The factor given in Table 1 is the ratio of surface resistance after x hours Suntest™ exposure to the surface resistance before the Suntest exposure.

TABLE 1

| Comparative Example nr | Condition of reaction medium prior to initiator addition | PEDOT/PSS type | PEDOT/PSS concentration [wt %] | Initial surface resistance [Ohm/square] | O.D. | Ratio of surface resistance after 48 h Suntest ™ exposure to initial surface resistance |
|---|---|---|---|---|---|---|
| 1 | no oxygen exclusion | P1 | 1.09 | 2900 | 0.067 | 83 |
| 2 | purged of oxygen by $N_2$ bubbling | P2 | 1.02 | 1200 | 0.066 | 13 |
| 3 | purged of oxygen by $N_2$ bubbling | P3 | 1.03 | 1200 | 0.065 | 12 |

The results in Table 1 show that the initial surface resistance and the stability of the PEDOT/PSS-layers is strongly dependent upon the conditions under which the polymerization is initiated, driving off oxygen by bubbling through with nitrogen resulting in lower surface resistance and higher stability to 48 h Suntest™ exposure as shown by lower ratios of surface resistance after Suntest' exposure to the initial surface resistance.

PREPARATION OF COPOLYMERS OF 3,4-ALKYLENEDIOXYTHIOPHENE AND 3,4-ALKYLENEDIOXYTHIOPHENEDIOXIDE COMPOUNDS

INVENTION EXAMPLES 1 TO 5

Dispersions of the copolymers of 3,4-alkylenedioxythiophene and 3,4-alkylenedioxythiophenedioxide compounds of INVENTION EXAMPLES 1 to 5 were prepared by mixing 39.5 g of a 6.01% by weight aqueous solution of poly (styrenesulphonic acid) [PSS] ($M_n$=ca. 40,000; $M_w$=290,000; degree of sulphonation >90%) with 170.5 g of deionized water and the quantities of EDOT and M1 given in Table 2 at 25° C. in a 500 mL reaction vessel equipped with a stirrer. This mixture was homogenized for 30 minutes with an ULTRATURRAX™ at 1000 rpm. 0.015 g $Fe_2(SO_4)_3$ and 1.79 g $Na_2S_2O_8$ were then added to initiate the copolymerization reaction. The reaction mixture was stirred at 25° C. for 7 h, after which a further 0.39 of $Na_2S_2O_8$ was added. After an additional reaction time of 16 h the reaction mixture was treated twice with ion exchanger (21 mL LEWATIT™ S100MB+35 mL LEWATIT™ M600MB from BAYER). The resulting mixture was additionally thermally treated at 95° C. for 2 h. This procedure yielded a dispersion of the copolymer (for type, quantity produced and concentrations of copolymer in the dispersion see Table 2).

TABLE 2

| | INVENTION EXAMPLE NUMBER | | | | |
|---|---|---|---|---|---|
| | 1 | 2 | 3 | 4 | 5 |
| EDOT wt [g] | 0.9 | 0.5 | 0.99 | 0.98 | 0.95 |
| EDOT [mmoles] | 6.33 | 3.52 | 6.96 | 6.89 | 6.68 |
| Comonomer | M1 | M1 | M1 | M1 | M1 |
| Comonomer wt [g] | 0.1 | 0.5 | 0.01 | 0.02 | 0.05 |
| Comonomer [mmoles] | 0.48 | 2.42 | 0.048 | 0.097 | 0.24 |
| Copolymer dispersion | CP1 | CP2 | CP3 | CP4 | CP5 |
| wt of (co)polymer dispersion prepared [g] | 123 | 79 | 135 | 140 | 132 |
| (co)polymer concentration in dispersion[wt %] | 1.02 | 1.03 | 1.49 | 1.40 | 1.41 |

Characterization of the homopolymers and copolymers of INVENTION EXAMPLES 1 to 5 and COMPARATIVE EXAMPLES 1 to 3:

The molecular weights of the homopolymers and copolymers of INVENTION EXAMPLES 1 TO 5 and COMPARATIVE EXAMPLES 1 to 3 were determined by aqueous gel permeation chromatography relative to sodium poly (styrene sulphonate) with UV-vis absorption detection at 785 nm.

The particle size of the copolymer/PSS latex particles in the dispersions were determined with a CPS Disc Centrifuge in which particle size distributions are determined using differential centrifugal sedimentation. Particles settle in a fluid under centrifugal field according to Stokes' Law. Sedimentation velocity increases as the square of the particle diameter, so particles that differ in size by only a few percent settle at significantly different rates. In differential sedimentation, all the particles in a sample begin sedimentation as a thin band. A sample of particles is placed on top of a column of clear liquid at the start of the analysis and the particles settle down in the centrifugal field. The detector initially reads maximum intensity, but the signal is reduced when particles reach the detector beam. The reduction in intensity indicates the concentration of particles in the detector beam. When a monochromatic light source is used, Mie theory light scattering can be applied to the intensity data to calculate the particle concentration. When all the particles have passed the detector, the signal returns to the original level. A plot of the particle concentration against the calculated particle diameter provides a differential distribution.

The molecular weights of the copolymers and PEDOT prepared in reaction media purged of oxygen by bubbling through with nitrogen prior to the addition of initiator together with their concentrations in the dispersions produced, the theoretical concentration in mol % in the comonomer and mean particle sizes are given in Table 3.

TABLE 3

| (Co) polymer nr. | Comonomer Nr. | Comonomer mol % | Concentration of copolymer/PSS [wt %] | mean particle size [nm] | molecular weight [785 nm] |
|---|---|---|---|---|---|
| P1 | — | 0 | 1.02 | 45 | 550,000 |
| P2 | — | 0 | 1.02 | 47 | 490,000 |
| P3 | — | 0 | 1.03 | 42 | 390,000 |
| CP1 | M1 | 7.05 | 1.02 | 52 | 260,000 |
| CP2 | M1 | 40.7 | 1.03 | 63 | 104,000 |
| CP3 | M1 | 0.68 | 1.49 | 138 | 230,000 |
| CP4 | M1 | 1.39 | 1.40 | 120 | 220,000 |
| CP5 | M1 | 3.47 | 1.41 | 88 | 230,000 |

PREPARATION OF LAYERS PREPARED WITH DISPERSIONS CONTAINING THE COPOLYMERS OF INVENTION EXAMPLES 1 TO 5

Coating dispersions were prepared with the dispersions of INVENTION EXAMPLES 1 to 5 as described above for the dispersions of COMPARATIVE EXAMPLES 1 to 3 so as to produce layer numbers 4 to 8, upon doctor blade-coating onto a subbed 175 μm poly(ethylene terephthalate) support and drying at 45° C. for 3.5 minutes, with the following composition:

| | |
|---|---|
| Copolymer of EDOT and M1 (or PEDOT) | 28.9 mg/m² |
| [copolymer of EDOT and M1 (or PEDOT)/PSS | 100 mg/m²] |
| ZONYL ™ FSO100 | 8 mg/m² |
| 3-glycidoxypropyl-trimethoxysilane | 100 mg/m² |
| copolymer latex of vinylidene chloride, methyl acrylate and itaconic acid (88/10/2) | 100 mg/m² |
| N-methyl pyrrolidinone | 2 mL/m² |

The surface resistance and optical density and the light stability of layer numbers 4 to 8 were determined as described above for layer numbers 1 to 3. The results are given in Table 4 together with those for layers 1 to 3.

TABLE 4

| Layer Nr | (Co)-polymer nr. | Layer containing (co)polymer | | |
|---|---|---|---|---|
| | | Comonomer nr. | mol % | Surface resistance [ohm/square] | O.D. |
| 1 | P1 | — | — | 3400 | 0.06 |
| 2 | P2 | — | 0 | 1200 | 0.066 |
| 3 | P3 | — | 0 | 1200 | 0.065 |
| 4 | CP1 | M1 | 7.05 | 3 × 10$^5$ | 0.06 |
| 5 | CP2 | M1 | 40.7 | >10$^{14}$ | 0.05 |
| 6 | CP3 | M1 | 0.68 | 2.6 × 10$^5$ | — |
| 7 | CP4 | M1 | 1.39 | 1.8 × 10$^5$ | — |
| 8 | CP5 | M1 | 3.47 | 7.7 × 10$^5$ | — |

PREPARATION OF LIGHT-EMITTING DEVICES 1 TO 3 WITH BAYTRON™ P EL AND THE COPOLYMERS OF INVENTION EXAMPLES 1 AND 2

Preparation of the Electroluminescent ZnS:Cu dispersion

The following solutions were prepared:

| Solution 1 | zinc acetate dihydrate | 131.7 g |
|---|---|---|
| | copper acetate monohydrate | 0.54 g |
| | deionized water | to 600 ml |
| Solution 2 | sodium sulphide nonahydrate | 113.6 g |
| | ammonia (50%) | 5 ml |
| | deionized water | to 600 ml |
| Solution 3 | TRI* | 40 g |
| | deionized water | to 1000 ml |
| | sodium chloride | 58.44 g |

*TRI = (5-methyl-1,2,4-triazolo-(1,5-a)-pyrimidine-7-ol)

Solutions 1 and 2 at room temperature were added simultaneously both at a flow rate of 500 ml/min to solution 3, held at room temperature and stirred at 1500 rpm. To 1000 ml of the resulting dispersion, 1000 ml of a 1% polyphosphoric acid solution adjusted to pH 6 with ammonium hydroxide was added and the dispersion was concentrated to 1000 ml by means ultrafiltration using a Fresenius F60 cartridge. This dispersion was subsequently diafiltrated by using 5500 ml of a 1% solution of polyphosphoric acid solution adjusted to pH 6 with ammonium hydroxide solution in water. The dispersion was further concentrated to a volume of about 570 ml to produce an aqueous dispersion at pH 6 containing 30 g/L ZnS:Cu and 1% polyphosphoric acid. The dispersion was then ball-milled for 1 hour. 20 ml of the resulting dispersion was then ultrasonically treated with a ultrasound bar (Vibra cell VCX 400 W from Sonics & Materials Inc.—amplitude about 78%—output 40%) for 3 minutes while cooling in ice. 3.2 g of a 5% by weight aqueous solution of poly(vinylpyrrolidinone) in water was then added to 16.8 g of the ZnS:Cu dispersion followed by further ultrasonic treatment with the ultrasound bar for 5 minutes. 0.5 ml of ZONYL™ FSO100 was then added as a 1% by weight aqueous solution followed by thorough stirring. The resulting dispersion was then filtered through a 5 μm MILLIPORE™ filter, a nano-dispersion of electroluminescent ZnS:Cu being thereby produced.

Preparation of a Patterned ITO Electrode:

An indium tin oxide [ITO] layer on 175 μm thick poly(ethylene terephthalate) [PET] from IST, with a surface resistance of about 80 Ohm/square, was used as the hole-conducting electrode. ITO/PET sheets of 5×5 cm$^2$ were taped off in the middle of the plate with a 2 cm Magic tape Scotch 810 from 3M. The sides of the ITO plates were then etched with a solution consisting of 50 mL of concentrated hydrochloric acid, 50 mL of deionized water and 4 mL of concentrated nitric acid. After the etching, the ITO/PET sheets were rinsed with water several times and subsequently dried with a hair dryer, dried, then put into a vessel with isopropanol which was itself put into an ultrasound bath for 10 minutes and finally dried at 50° C. for 10 minutes. Each ITO/PET sheet contained a band of 2 cm of conductive ITO in the middle.

Preparation and Application of the Hole Injecting and Electron Blocking Layer:

The copolymer dispersions CP06 and CP07, with M1-EDOT-copolymers containing 7.05 and 40.7 mol % M1 respectively, were prepared analogously to those of CP01 and CP02, but each with concentrations of copolymer/PSS of 1.2% by weight instead of 1.02 and 1.03% by weight respectively.

Dispersion numbers 1 to 3, given in Table 5, were then prepared using BAYTRON™ P EL from BAYER containing 1.2% by weight of PEDOT/PSS with a PEDOT:PSS weight ratio of 1:2.4 (=P4) and copolymer dispersions CP06 and CP07.

TABLE 5

| Dispersion nr | (Co)-polymer dispersion nr. | quantity [g] | quantity of 5% aqueous solution of ZONYL® FSO100 [mL] | pH of dispersion |
|---|---|---|---|---|
| 1 | P4 | 7.5 | 3 | 1.98 |
| 2 | CP6 | 7.5 | 3 | 2.01 |
| 3 | CP7 | 7.5 | 3 | 2.10 |

Solutions 1, 2 and 3 were spincoated onto patterned ITO/PET sheets for 6s at 800 rpm followed by 50s at 1500 rpm. The resulting layers were dried at 50° C. for 10 minutes giving a layer thickness of about 100 nm thereby producing the substrates 1, 2 and 3 respectively.

The thicknesses were measured with a DEKTAK™ profilometer with the layer spincoated on glass. Similar layer thicknesses can be expected on ITO/PET.

Coating with the ZnS:Cu Electroluminescent Dispersion:

The above-described electroluminescent nano ZnS:Cu-dispersion was spincoated onto substrates 1, 2 and 3 respectively for 6 seconds at 1000 rpm followed by 50 seconds at 2000 rpm followed by drying at 50° C. for 10 minutes, thereby producing electroluminescent ZnS:Cu-layers with a thickness of 100 nm.

Figure 1:
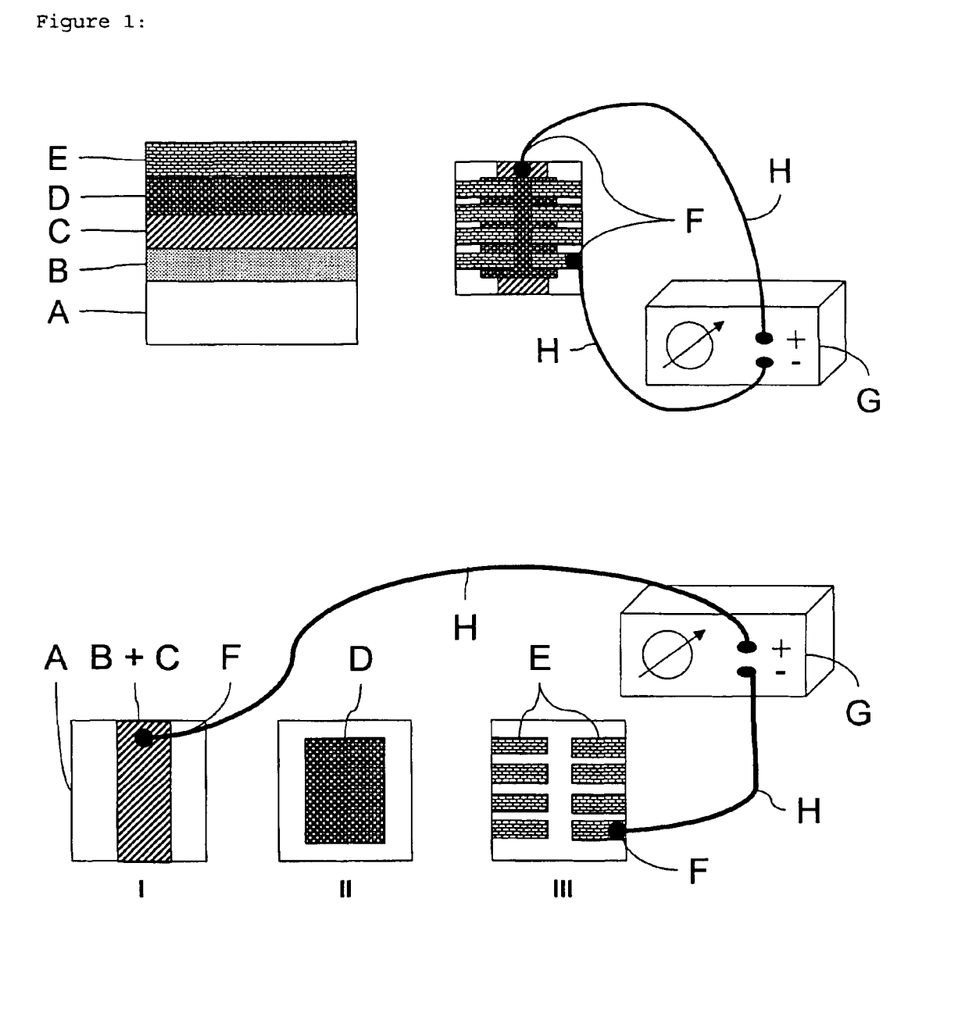

Application of the Aluminium Electrode:

Subsequently, a 160 nm thick aluminium electrode (cathode) was vacuum deposited on the spincoated electroluminescent ZnS:Cu-layers at a vacuum of 1.33×10$^{-4}$ N m$^{-2}$ Pa using a mask to produce light emitting devices 1 to 3 respectively with the device construction shown in FIG. 1. The emission area was 25 mm$^2$.

Performance of Light Emitting Devices 1 to 3:

The electroluminescence results of light emitting devices 1 to 3 are given in Table 6. With forward bias, the devices exhibited electroluminescence with a λmax of 490 nm. For the lifetime measurements, a forward bias was applied and the voltage was increased so as to maintain the light output constant at ca. 0.5 Cd/m$^2$. The maximum applied voltage was 12 V. The lifetime of the light emitting device was taken to be the time between the application of the optimum voltage and the moment no further electroluminescence could be observed. The optimum voltage was that voltage at which maximum light output was observed.

TABLE 6

| Device nr. | Hole injecting and electron blocking layer | Optimum voltage (V) | Electroluminescence lifetime [s] |
|---|---|---|---|
| 1 (Comparison) | P4 + ZONYL ™ FSO100 | 6.9 | 390 |
| 2 (Invention) | CP6 (EDOT-M1-copolymer with a molar ratio of 92.95:7.05) + ZONYL ™ FSO100 | 6.5 | 675 |
| 3 (Invention) | CP7 (EDOT-M1-copolymer with a molar ratio of 59.3:40.7) + ZONYL ™ FSO100 | 5.5 | 860 |

From Table 6 it can be concluded that the optimum voltage for the block copolymer of PEDOT-PEDOT-dioxide was lower compared with the BAYTRON® P EL hole transporting material, which is normally used. This probably accounts for the longer electroluminescence lifetimes observed, because a lower mean voltage is necessary to maintain the light output at a constant level.

PREPARATION OF DEVICES 4 TO 6 WITH BAYTRON® P EL AND THE COPOLYMERS OF INVENTION EXAMPLES 1 AND 2 AND AN ORGACON™ EL300-ANODE

In the light-emitting devices 4 to 6, the transparent conductive film ORGACON™ EL300 [a coating comprising PEDOT/PSS on a PET substrate], commercially available from AGFA-GEVAERT N.V., was used as an anode instead of ITO-PET. The ORGACON™ EL300 foil was cut into 5 cm×5 cm samples. The resist AZ7217 (from CLARIANT) was then spincoated onto the PEDOT/PSS-coating and baked for 30 minutes at 90° C. giving a dry layer thickness of 2–3 µm. The ORGACON™ EL300 film coated with AZ7217 was then exposed with UV-light of intensity 4 mW/cm² through a mask for ca. 60 s, in order to illuminate the middle part (5 cm×2 cm) of the resist to obtain the same pattern as for the ITO-PET described above, followed by a prebake for 45 seconds at 110° C. and 40 s development in the AZ351B developer (from CLARIANT). In order to obtain good adhesion a 30 minute pre-exposure bake at 110° C. was necessary. The areas from which the resist was thereby removed were deactivated by dipping the sample in a 1% NaClO solution for 20 seconds. This step was followed by rinsing with water and drying. The foils were then integrally exposed to UV-light with an intensity of 4 mW/cm² for 60 s and the resist removed by developing in isopropanol for 90 seconds. The foils were then washed with water and dried. The resulting foils consisted of a conductive area (ca. 300 Ω/square) in the middle of the material with dimensions 5 cm×2 cm.

The thus patterned ORGACON™ EL300 foils were coated with above-described dispersions 1 to 3 respectively for 6 s at 800 rpm followed by 50 s at 1500 rpm. The resulting layers were dried at 50° C. for 10 minutes. This resulted in a layer thickness of about 100 nm thereby producing substrates 4, 5 and 6 respectively. The thicknesses were measured with a DEKTAK™ profilometer with the layer spincoated on glass. Similar layer thicknesses can be expected on PEDOT/PET.

Substrates 4 to 6 were then coated with the electroluminescent nano ZnS:Cu-dispersion and an aluminium cathode as described above for light-emitting devices 1 to 3, thereby producing light-emitting devices 4 to 6 respectively.

The electroluminescence results of light emitting devices 1 to 3 obtained as described for light-emitting devices 1 to 3, except that the voltage was increased so as to maintain the light output constant at ca. 0.1 Cd/m² instead of about 0.5 Cd/m², are given in Table 7.

TABLE 7

| Light emitting device nr. | Hole injecting and electron blocking layer | Optimum voltage (V) | Electroluminescence lifetime [s] |
|---|---|---|---|
| 4 (Comparison) | P4 + ZONYL ™ FSO100 | 6.6 | 720 |
| 5 (Invention) | CP6 (EDOT-M1-copolymer with a molar ratio of 92.95:7.05) + ZONYL ™ FSO100 | 6.3 | 1260 |
| 6 (Invention) | CP7 (EDOT-M1-copolymer with a molar ratio of 59.3:40.7) + ZONYL ™ FSO100 | 5.4 | not determined |

From Table 7 it can be concluded that the optimum voltage for the block copolymer of PEDOT-PEDOT-dioxide was lower compared with the BAYTRON® P EL hole transporting material, which is normally used. This probably accounts for the longer electroluminescence lifetime observed in the case of light-emitting device 5, because a lower mean voltage was necessary to maintain the light output at a constant level.

COMPARATIVE EXAMPLE 4 AND INVENTION EXAMPLES 6–21

Oxidation experiments were carried out by adding different quantities of meta-chloroperbenzoic acid (m-CPBA) to 100 mL of a 1.05 wt % aqueous dispersion of PEDOT/PSS and stirring the resulting mixture for 2 h at 25° C. The resulting dispersions were then doctor blade-coated in a standard composition to a standard thickness on a subbed PET support and the surface resistance of the resulting layers determined. The quantities of m-CPBA added, the molar quantity with respect to the PEDOT present and the resulting surface resistance are given in Table 8.

These experiments demonstrate the possibilities of producing an electronductive pattern by patternwise treatment of PEDOT/PSS-layers with an oxidizing agent such as meta-chloroperbenzoic acid.

TABLE 8

| | m-CBPA added | | Surface resistance at 25° C. and |
|---|---|---|---|
| | wt. in [mg] | moles/mole PEDOT | 30% RH [Ω/square] |
| Comparative Example nr | | | |
| 4 | 0 | 0 | $1.8 \times 10^3$ |
| 5 | 5.1 | 0.01 | $1.9 \times 10^3$ |
| 6 | 10.2 | 0.02 | $1.7 \times 10^3$ |
| 7 | 25.5 | 0.05 | $1.8 \times 10^3$ |
| 8 | 51 | 0.10 | $2.0 \times 10^3$ |
| 9 | 102 | 0.20 | $2.6 \times 10^3$ |
| 10 | 255 | 0.50 | $5.9 \times 10^3$ |
| 11 | 510 | 1.00 | $2.2 \times 10^4$ |
| 12 | 766 | 1.50 | $7.8 \times 10^4$ |
| 13 | 1021 | 2.00 | $4.7 \times 10^5$ |
| Invention Example nr. | | | |
| 6 | 1530 | 300 | $1.0 \times 10^9$ |

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A 3,4-alkylenedioxythiophenedioxide compound represented by formula (I):

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

2. Compound according to claim 1, wherein said compound is 2,3-dihydro-thieno[3,4-] [1,4]dioxine 6,6-dioxide.

3. A polymer comprising monomeric units of at least one compound represented by formula (I):

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

4. Polymer according to claim 3, wherein said polymer further comprises monomeric units of at least one thiophene or pyrrole compound.

5. Polymer according to claim 3, wherein said polymer further comprises monomeric units of a at least one 3,4-alkylenedioxythiophene compound.

6. Polymer according to claim 3, wherein said polymer further comprises monomeric units of at least one 3,4-alkylenedioxythiophene compound represented by formula (II):

in which: A' represents a $C_{1-5}$-alkylene bridge; R' represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

7. Polymer according to claim 5, wherein said 3,4-alkylenedioxythiophene compound is selected from the group consisting of: 3,4-ethylenedioxythiophene, 3,4-propylenedioxythiophene, 3,4-dihydro-2H-thieno[3,4-b][1,4]dioxin-2-yl)methanol, 3,4-dihydro-2H-thieno[3,4-b][1,4]dioxepin-3-ol, (2,3-dihydro-thieno[3,4-b][1,4]dioxin-2-ylmethoxy)-acetic acid ethyl ester, (2,3-dihydro-thieno[3,4-b][1,4]dioxin-2-yl-methoxy)-acetic acid, 2-{2-[2-(2-methoxy-ethoxy)-ethoxy]-ethoxymethyl}-2,3-dihydro-thieno[3,4-b][1,4]dioxine and 4-(2,3-dihydro-thieno[3,4-b][1,4]dioxin-2-ylmethoxy)-butane-1-sulphonic acid sodium salt.

8. Polymer according to claim 5, wherein said 3,4-alkylenedioxythiophene compound is 3,4-ethylenedioxythiophene.

9. An aqueous dispersion of a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group; and a polyanion.

10. Aqueous dispersion according to claim 9, wherein said polymer further comprises monomeric units of at least one thiophene or pyrrole compound.

11. Aqueous dispersion according to claim 9, wherein said polymer further comprises monomeric units of at least one 3,4-alkylenedioxythiophene compound.

12. Aqueous dispersion according to claim 9, wherein said polyanion is poly(styrenesulphonic acid).

13. A chemical polymerization process for preparing an aqueous dispersion according to claim 9 comprising the steps of: (i) providing a solution of a polyanion; (ii) adding a compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group and at least one thiophene or pyrrole compound to the solution provided in step (i); and (iii) adding an oxidizing or reducing system to the mixture provided in step (ii).

14. Chemical polymerization process according to claim 13, wherein said thiophene or pyrrole compound is a 3,4-alkylenedioxythiophene compound.

15. A process for using an aqueous dispersion of a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group, and a polyanion; for coating an object.

16. A printable paste containing an aqueous dispersion of a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group; and a polyanion.

17. An electroconductive layer containing a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

18. A process for using an electroconductive layer containing a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group, in a light emitting diode.

19. An antistatic layer containing a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

20. An electroconductive pattern comprising a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group.

21. A process for preparing an electroconductive pattern comprising a polymer comprising monomeric units of at least one compound represented by formula (I):

(I)

in which: A represents a $C_{1-5}$-alkylene bridge; R represents an optionally substituted $C_{1-24}$-alkyl, $C_{3-18}$-cycloalkyl, $C_{1-18}$-alkoxy or polyethylene oxide group (optionally with at least one substituent selected from the group consisting of an alcohol, amide, ether, ester or sulphonate group) or an optionally substituted aryl group, comprising the steps of: providing a layer of a polymer containing 3,4-alkylenedioxythiophene monomer units; and pattern-wise oxidizing said polymer containing 3,4-alkylenedioxythiophene monomer units to polymers containing 3,4-alkylenedioxythiophenedioxide monomer units.

* * * * *